(12) United States Patent
Asleson et al.

(10) Patent No.: US 10,350,387 B2
(45) Date of Patent: Jul. 16, 2019

(54) IMPLANT TOOL FOR SUBSTERNAL OR PERICARDIAL ACCESS

(71) Applicant: Medtronic Inc., Minneapolis, MN (US)

(72) Inventors: Andrea J. Asleson, Maple Grove, MN (US); Melissa G. T. Christie, Andover, MN (US); Amy E. Thompson-Nauman, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 386 days.

(21) Appl. No.: 14/293,260

(22) Filed: Jun. 2, 2014

(65) Prior Publication Data

US 2015/0343176 A1 Dec. 3, 2015

(51) Int. Cl.
*A61M 25/01* (2006.01)
*A61B 17/32* (2006.01)
*A61M 25/00* (2006.01)
*A61N 1/05* (2006.01)
(Continued)

(52) U.S. Cl.
CPC . *A61M 25/0152* (2013.01); *A61B 17/320016* (2013.01); *A61B 17/3415* (2013.01); *A61B 17/3468* (2013.01); *A61M 25/008* (2013.01); *A61N 1/05* (2013.01);
(Continued)

(58) Field of Classification Search
CPC ............ A61M 25/008; A61M 25/0152; A61M 25/0194; A61M 25/0133; A61M 25/0144; A61M 25/0147; A61M 2025/0081; A61B 17/320016; A61B 17/3415; A61B 17/3468; A61B 2017/00318; A61B 2017/00323; A61B 2017/00331; A61B 2017/320056
See application file for complete search history.

(56) References Cited

U.S. PATENT DOCUMENTS 2,541,402 A * 2/1951 Caine ................... A61B 1/2676
128/200.26
3,452,742 A * 7/1969 Muller .................. A61B 10/04
600/434
(Continued)

FOREIGN PATENT DOCUMENTS

EP 2252365 B1 10/2013
WO 2007126632 A2 11/2007
(Continued)

OTHER PUBLICATIONS (PCT/US2015/033119) PCT Notification of Transmittal of the International Search Report and the Written Opinion of the International Searching Authority, dated Aug. 14, 2015, 11 pages.
(Continued)

*Primary Examiner* — Alexander J Orkin

(57) ABSTRACT

A medical device and medical method. The medical device includes a flexible elongate body defining a proximal end and a distal end. The elongate body defines a first lumen spanning from the proximal end to a location proximal to the distal end. A shaping member insertable within the first lumen is included, the shaping member is configured to retain a manipulated shape when the flexible elongate body is manipulated from a first configuration to a second configuration. A tip is coupled to the distal end.

12 Claims, 5 Drawing Sheets

(51) Int. Cl.
*A61B 17/34* (2006.01)
*A61B 17/00* (2006.01)

(52) U.S. Cl.
CPC ........... *A61B 2017/00331* (2013.01); *A61B 2017/320056* (2013.01); *A61M 25/0194* (2013.01); *A61M 2025/0081* (2013.01)

(56) References Cited

U.S. PATENT DOCUMENTS

| | | | | |
|---|---|---|---|---|
| 3,605,725 | A * | 9/1971 | Bentov | A61B 1/0052 600/434 |
| 3,719,737 | A | 3/1973 | Vaillancourt et al. | |
| 4,033,331 | A * | 7/1977 | Guss | A61M 25/0041 600/434 |
| 4,808,157 | A | 2/1989 | Coombs | |
| 5,231,989 | A * | 8/1993 | Middleman | A61B 1/00165 600/434 |
| 5,308,318 | A * | 5/1994 | Plassche, Jr. | A61M 25/0147 604/540 |
| 5,376,084 | A * | 12/1994 | Bacich | A61M 25/0041 604/515 |
| 5,487,757 | A * | 1/1996 | Truckai | A61B 18/1492 604/264 |
| 5,628,734 | A | 5/1997 | Hatfalvi | |
| 5,700,252 | A * | 12/1997 | Klingenstein | A61M 25/0068 604/264 |
| 5,746,202 | A | 5/1998 | Pagan | |
| 5,807,324 | A * | 9/1998 | Griffin, III | A61B 18/1492 604/264 |
| 5,919,183 | A | 7/1999 | Field | |
| 6,003,510 | A | 12/1999 | Anunta | |
| 6,119,695 | A | 9/2000 | Augustine et al. | |
| 6,126,649 | A * | 10/2000 | VanTassel | A61M 25/0147 604/528 |
| 6,656,166 | B2 | 12/2003 | Lurie et al. | |
| 6,749,574 | B2 | 6/2004 | O'Keefe | |
| 7,008,442 | B2 | 3/2006 | Brightbill | |
| 8,029,495 | B2 * | 10/2011 | Pyles | A61M 25/0041 604/164.13 |
| 8,048,030 | B2 | 11/2011 | McGuckin, Jr. et al. | |
| 2002/0173785 | A1 * | 11/2002 | Spear | A61B 18/1492 606/41 |
| 2004/0116848 | A1 * | 6/2004 | Gardeski | A61M 25/0147 604/95.01 |
| 2004/0138570 | A1 * | 7/2004 | Nita | A61B 17/320068 600/466 |
| 2005/0049574 | A1 * | 3/2005 | Petrick | A61M 25/0026 604/525 |
| 2005/0149062 | A1 * | 7/2005 | Carroll | A61B 17/3478 606/129 |
| 2005/0277889 | A1 | 12/2005 | Neidert et al. | |
| 2006/0004324 | A1 | 1/2006 | Ruddell et al. | |
| 2007/0142842 | A1 * | 6/2007 | Krueger | A61B 17/8811 606/92 |
| 2008/0046056 | A1 | 2/2008 | O'Connor | |
| 2008/0249420 | A1 * | 10/2008 | Crossman | A61M 25/0068 600/481 |
| 2009/0131950 | A1 * | 5/2009 | Liu | A61B 17/8811 606/94 |
| 2011/0224713 | A1 | 9/2011 | Fortson | |
| 2012/0016377 | A1 | 1/2012 | Geroy | |
| 2012/0029335 | A1 | 2/2012 | Sudam et al. | |
| 2012/0089141 | A1 * | 4/2012 | Lee | A61B 18/1477 606/41 |
| 2012/0130381 | A1 * | 5/2012 | Germain | A61B 17/1642 606/84 |
| 2012/0204867 | A1 | 8/2012 | Levitan | |
| 2014/0094645 | A1 | 4/2014 | Lafontaine et al. | |

FOREIGN PATENT DOCUMENTS

| | | |
|---|---|---|
| WO | 2014151160 A1 | 9/2014 |
| WO | 2015073480 A1 | 5/2015 |

OTHER PUBLICATIONS

Ganapathy et al., "Implantable Device to Monitor Cardiac Activity with Sternal Wires," Pace, vol. 37, Dec. 2014, 11 pp.

Guenther, et al., "Substernal Lead Implantation: A Novel Option to Manage DFT Failure in S-ICD patients," Clinical Research Cardiology, Published On-line Oct. 2, 2014, 3 pages.

Tung et al., "Initial Experience of Minimal Invasive Extra Cardiac Placement of High Voltage Defibrillator Leads," Canadian Cardiovascular Congress 2007, Oct. 2007, vol. 23, Supplement SC, Abstract 0697, http://www.pulsus.com/ccc2007/abs/0697.htm, 2 pages.

Donald Nuss, MB, ChB Frcs(c), FACS, FAAP, Recent Experiences with Minimally Invassive Pectus Excavatum Repair "Nuss Procedure", The Japanese Journal of Thoracic and Cardiovascular Surgery, 2005, pp. 338-344.

E. Cigna, et al., A new technique for substernal colon transposition with a breast dissector: Report of 39 cases, Journal of Plastic, Reconstructive & Aesthetic Surgery (2006) 59, pp. 343-346.

Medtronic, 6996T Tunneling Tool, Technical Manual, UCX19842001 198462001, Sep. 2001.

LMA, Airway Management, LMA Product Accessories, http://www.lmana.com/pwpcontrol.php?pwpID=4496.

National Tracheostomy Safety Project, Advanced Algorithm, http://www.tracheostomy.org.uk/Tracheostomy/New%20Blue%20Trachy%20Webpages/Advanced%20Algorithm%202.htm.

* cited by examiner

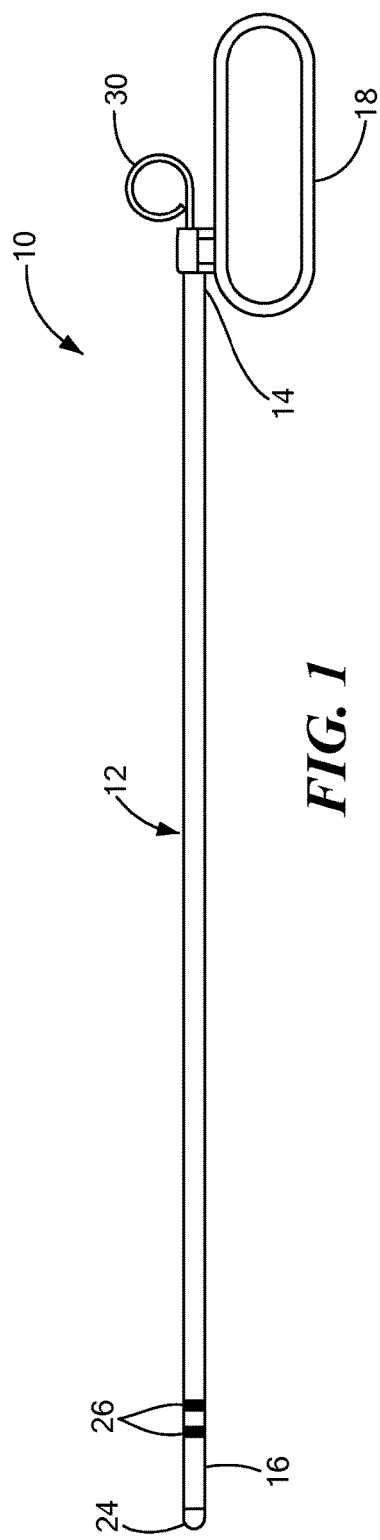
FIG. 1
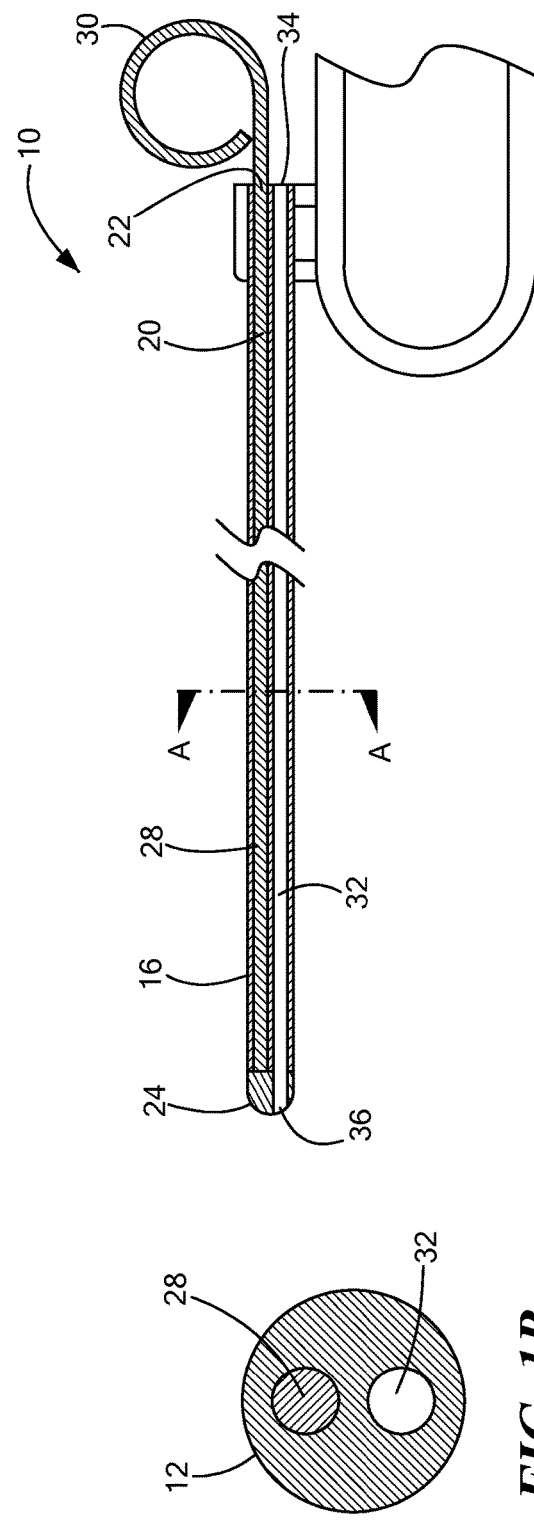
FIG. 1A
FIG. 1B

IMPLANT TOOL FOR SUBSTERNAL OR PERICARDIAL ACCESS

CROSS-REFERENCE TO RELATED APPLICATION n/a

STATEMENT REGARDING FEDERALLY SPONSORED RESEARCH OR DEVELOPMENT n/a

FIELD OF THE INVENTION

The present application relates to methods and medical devices for creating a substernal pathway for implantation of a medical lead.

BACKGROUND OF THE INVENTION

Malignant tachyarrhythmia, for example, ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes.

In patients at high risk of ventricular fibrillation, the use of an implantable cardioverter defibrillator (ICD) system has been shown to be beneficial at preventing SCD. An ICD system includes an ICD, which is a small battery powered electrical shock device, may include an electrical housing, or can electrode, that is coupled to one or more electrical lead wires placed within the heart. If an arrhythmia is sensed, the ICD may send a pulse via the electrical lead wires to shock the heart and restore its normal rhythm. Owing to the inherent surgical risks in attaching and replacing electrical leads directly within or on the heart, methods have been devised to achieve a similar effect to that of a transvenous ICD system connected directly to the heart without placing electrical lead wires within the heart or attaching electrical wires directly to the heart.

Extravascular medical leads and systems, for example, subcutaneous implantable cardioverter-defibrillator (SubQ ICD) systems, have been devised to deliver electrical impulses to the heart by the use of a defibrillation lead placed subcutaneously above the ribcage and/or sternum of the patient. However, when gaining subcutaneous or substernal access to the torso for insertion of medical leads or other medical devices, it is beneficial to have tools specifically suited to accessing the anatomical space to achieve repeatable, atraumatic access. Indeed, in the absence of appropriate tools, physicians may use their fingers or forceps for blunt dissection to access the necessary anatomy, which can cause wounds, tissue damage or affect overall healing time.

SUMMARY OF THE INVENTION

The present application advantageously provides for a medical device and medical method for obtaining substernal or pericardial access. The medical device includes a flexible elongate body defining a proximal end and a distal end. The elongate body defines a first lumen spanning from the proximal end to a location proximal to the distal end. A shaping member insertable within the first lumen is included, the shaping member is configured to retain a manipulated shape when the flexible elongate body is manipulated from a first configuration to a second configuration. A tip is coupled to the distal end.

In another embodiment, the method includes manipulating an elongate flexible body from a first substantially linear configuration to a second substantially curvilinear configuration. The elongate flexible body is advanced in the second substantially curvilinear configuration from a first location proximate the xiphoid process to a second location posterior to the inferior end of the sternum.

In yet another embodiment, the medical device includes a flexible elongate body defining a proximal end and a distal end. The elongate body defines a first lumen spanning from the proximal end to a location proximal to the distal end, and a second lumen spanning from the proximal end out through the distal end. A shaping member is included affixed within the first lumen, the shaping member configured to retain a manipulated shape when the flexible elongate body is manipulated from a first configuration to a second configuration. A tip is molded to the distal end, the tip is sized to close at least the first lumen. The flexible elongate body has a first durometer of hardness, and the tip has a second durometer of hardness less than the first durometer of hardness

BRIEF DESCRIPTION OF THE DRAWINGS

A more complete understanding of the present application, and the attendant advantages and features thereof, will be more readily understood by reference to the following detailed description when considered in conjunction with the accompanying drawings wherein:

FIG. 1 is a side view of an exemplary tunneling tool constructed in accordance with the principles of the present application;

FIG. 1A is a side cross-sectional view of the tunneling tool shown in FIG. 1;

FIG. 1B is cross-sectional view of the tunneling tool shown in FIG. 1A across section A-A;

DETAILED DESCRIPTION OF THE INVENTION

Figure 2:
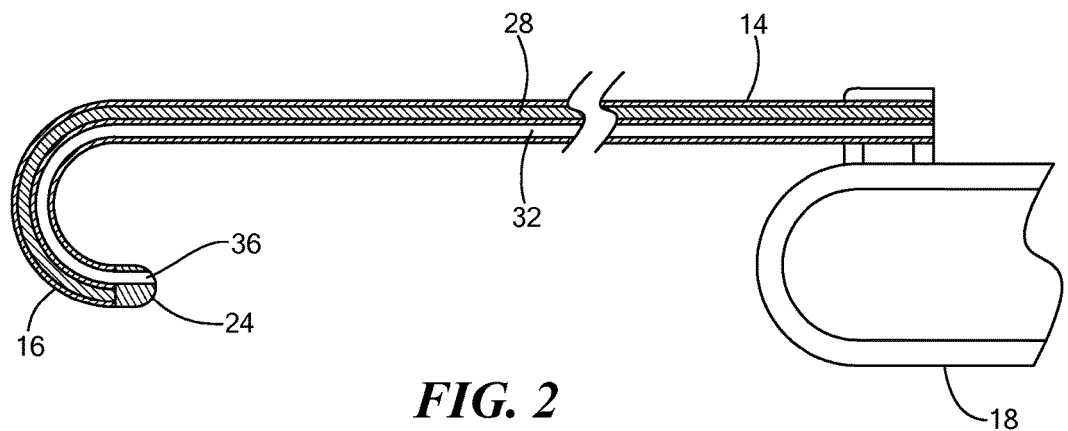
FIG. 2 is a side-cross sectional view of the tunneling tool shown in FIG. 1 in a manipulated configuration.

Referring now to the drawings in which like reference designators refer to like elements, there is shown in FIGS. 1-1B an exemplary medical device constructed in accordance with the principles of the present application and designated generally as "10." The medical device 10 may include a tunneling tool 12 sized to be received within the torso of a human or animal patient. In particular, the tunneling tool 12 may be an elongate solid or hollow body, sized and configured to penetrate the fascia and the anterior mediastinum proximate the xiphoid process. The tunneling tool 12 may include a proximal portion 14 and a distal portion 16 joined together and continuous along the length of the tunneling tool 12. The proximal portion 14 may be coupled to a handle 18, which may be any shape or size sufficient for the surgeon to grip. In an exemplary configuration the handle 18 defines a closed loop. The tunneling tool 12 may define an outer diameter of, for example, 0.1 to 0.3 inches.

The tunneling tool 12 may be composed of at least in part, an extruded thermoplastic polymer such as polyether block amide, high-density polyethylene (HDPE), or any other materials whether extruded or non-extruded, such that the tunneling tool 12 is flexible. Alternatively, any flexible material may be used to impart flexibility onto the tunneling tool 12, for example, a biocompatible metal or alloy such as Nitinol. In other configurations, the proximal portion 14 of the tunneling tool 12 may be substantially rigid and inflexible, while the distal portion 16 may be flexible. For example, the proximal portion 14 may be composed of a rigid stainless steel and the distal portion 16 may be composed of suitable flexible materials. In one configuration, the proximal portion 14 of the tunneling tool 12 is joined to the distal portion 16 of the tunneling tool 12 at approximately the midpoint of the tunneling tool 12 with the proximal portion 14 being rigid and the distal portion 16 being flexible. The two portions may be adjoined at other locations along the length of the body of tunneling tool 12.

The tunneling tool 12 may define a first lumen 20 spanning from the proximal end of the proximal portion 14 to a position proximal the distal end of the distal portion 16. The first lumen 20 may be substantially coaxial with the major longitudinal axis of the tunneling tool 12 such that the center of the first lumen 20 is coextensive with center of the tunneling tool 12. In other configurations, the first lumen is off-set from the center of the tunneling tool 12. The proximal end of the first lumen 20 may define a first opening 22 facilitating access to the first lumen 20 from the proximal end. The distal end of the first lumen 20 may be closed by a tip 24. The tip 24 may be an integral part of the elongate body of tunneling tool 12 in some embodiments. In other instances, the tip 24 may be coupled or otherwise attached to the distal end of the tunneling tool 12. In an exemplary configuration, the tip 24 is molded to the distal end of the tunneling tool 12. The tip 24 defines an atraumatic surface so as to reduce damage to tissue when traversing a patient's anatomy. For example, the tip 24 may be composed of a softer material with a lower durometer hardness compared to a higher durometer hardness material of the remainder of the elongate body of the tunneling tool 12. The tip 24 may define a quarter-spherical shape, hemi-spherical, or any blunted shape, to close off the first lumen 20. In other configurations, the first lumen 20 may extend through the tip 24 such that tip 24 defines a second opening (not shown) such that the first lumen 20 is accessible from both the first opening 22 and the second opening. Proximal to the tip 24 may be one more radiopaque markers 26 such that the distal portion 16 may be seen under fluoroscopy.

Continuing to refer to FIGS. 1A-B in an exemplary configuration, the first lumen 20 defines a circular cross-sectional area and is sized to slideably receive a shaping member 28. The shaping member 28 may be a stainless steel mandrel removeably insertable within the first lumen 20. In one configuration, the shaping member 28 is inserted into the first opening 22 and slid the entire length of the first lumen 20. The shaping member 28 may substantially fill the entire volume of the first lumen 20, such that it may be friction fit within the first lumen 20, or alternatively be loosely fit within the first lumen 20, such that it may readily be removed. In other configurations, the shaping member 28 may be permanently affixed within the first lumen 20 by being molded or otherwise bonded within the firm lumen 20. In alternative embodiments, shaping member 28 may be other malleable materials beside a stainless steel mandrel, including, but not limited to metals or alloys containing aluminum, silver, iron, copper, tin, lithium, or indium.

Continuing to refer FIGS. 1A-1B, to facilitate multiple configurations of the tunneling tool 12, the shaping member 28 may include a grip 30 at its proximal end that extends outward from the first opening 22. The grip 30 may be ring shaped such that the user may pull on the grip 30 with a single finger. In configurations in which the shaping member 28 is removable, the user may advance or retract the shaping member 28 to a desired location by pushing or pulling on the grip 30. For example, the user may advance the shaping member 28 to any location within the first lumen 20, for example, approximately the midpoint of the first lumen 20, to provide for additional configurations the tunneling tool 12 may be manipulated into by the user.

Referring now to FIG. 2, the shaping member 28 may include material properties that enable the user of the tunneling tool 12 to manipulate the tunneling tool 12 into desired configurations. In particular, the shaping member 28 may be malleable such that it retains its shape when manipulated from a first configuration to a second configuration. For example, the shaping member 28 may be retained within the first lumen 20 such that the tunneling tool 12 may initially define a substantially linear configuration. The user may manipulate, for example, the distal portion 16 of the tunneling tool 12 such that the distal portion 16 may define a curved, arcuate, helical, or be disposed in an otherwise bent configuration. The tunneling tool 12 retains this second configuration until the shaping member 28 is manipulated to another configuration by the user. The shape of the second configuration may depend on the desired use of the tunneling tool 12. For example, to gain access to the substernal space proximate the xiphoid process, the user may desire to bend the distal portion 16 to posteriorly tunnel around the tough diaphragmatic attachments subjacent the xiphoid process. The user may then desire to have a substantially linear tunneling tool 12 to tunnel from the inferior end of the sternum to a position proximate the superior end of the sternum. Alternatively, the user may advance the tunneling tool 12 in its bent configuration such that the tip 24, which is atraumatic, may be slid along the posterior surface of the sternum toward the superior end of the sternum, thus reducing damage to tissue, such as the lungs. Thus, the tunneling tool 12 as a whole may have a multitude of applications by manipulation of the shaping member 28 to various configurations.

Referring now to FIGS. 1-2, the tunneling tool 12 may define a second lumen 32 spanning from the proximal end of the proximal portion 14 of the tunneling tool 12 out through the distal end of the distal portion 16. The second lumen 32 may be at least substantially isodiametric to that of the first lumen 20 such that the shaping member 28 may be slideably receivable within either the first lumen 20 or the second lumen 32. For example, both the first lumen 20 and the second lumen 32 may define a diameter of approximately 0.040 inches, and either of the first lumen 20 and the second lumen 32 may range in diameter from 0.02 inches to 0.10 inches in diameter depending on the particular application for each respective lumen. For example, in other configurations, the second lumen 32 defines a larger or smaller diameter to that of first lumen 20 and may define a particular cross-sectional shape to accommodate the insertion of different medical devices. For example, the second lumen 32 may define a hemispherical cross-section of approximately 0.05 inches to accommodate an 18g needle, a smaller diameter than that of the first lumen 20 to accommodate a guidewire, or a larger diameter than that of the first lumen 20 to accommodate the perfusion of fluid. In an exemplary configuration, the first lumen 20 and the second lumen 32 are substantially equally spaced apart from each other within the tunneling tool 12. The second lumen 32 may define a third opening 34 proximate the handle 18 and a fourth opening 36 at the distal end of the distal portion 16.

Figure 3:
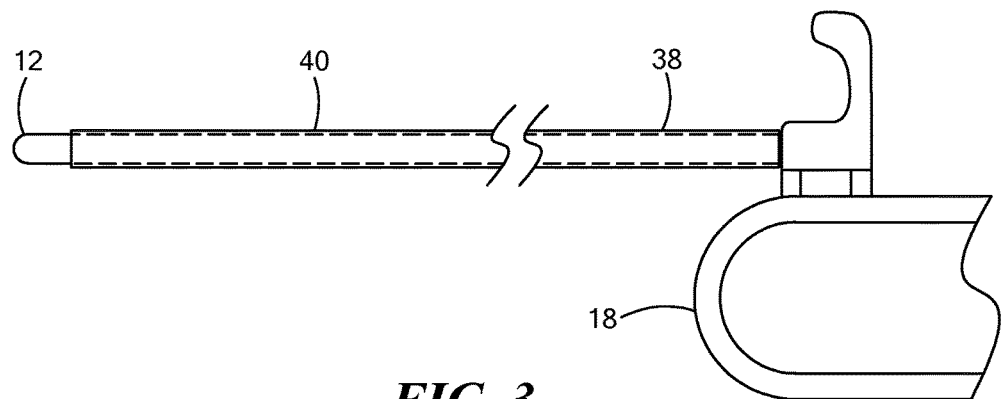
FIG. 3 is a side view of the tunneling tool shown in FIG. 1 with a sheath disposed around its exterior.

Referring to FIG. 3, an introducer sheath 38 may be disposed around the circumference of the tunneling tool 12. The sheath 38 may include a scoring 40 on its outer surface such that the sheath may be peeled off from the tunneling tool 12 when the tunneling tool 12 is advanced or retracted to a desired location. In another embodiment, the sheath 38 may be an open sheath as described in U.S. patent application Ser. No. 14/196,298, filed Mar. 4, 2014 and entitled "EXTRAVASCULAR IMPLANT TOOLS WITH OPEN SHEATH AND IMPLANT TECHNIQUES UTILIZING SUCH TOOLS." The entire content of this application describing the open sheath is expressly incorporated herein by reference. In other embodiments, the tunneling tool 12 may be advanced through the introducer sheath 38 which is placed by a dilator proximate the xiphoid process.

Figure 4:
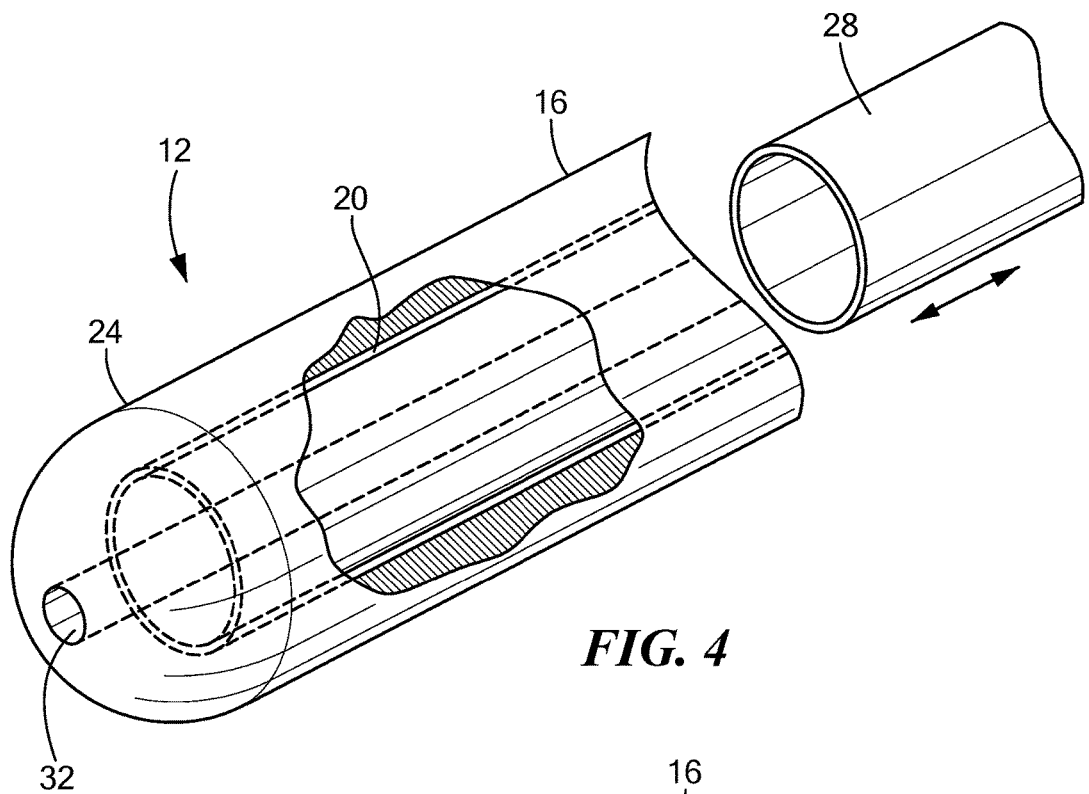
FIG. 4 is a side perspective view of another tunneling tool constructed in accordance with the principles of the present application.
Figure 5:
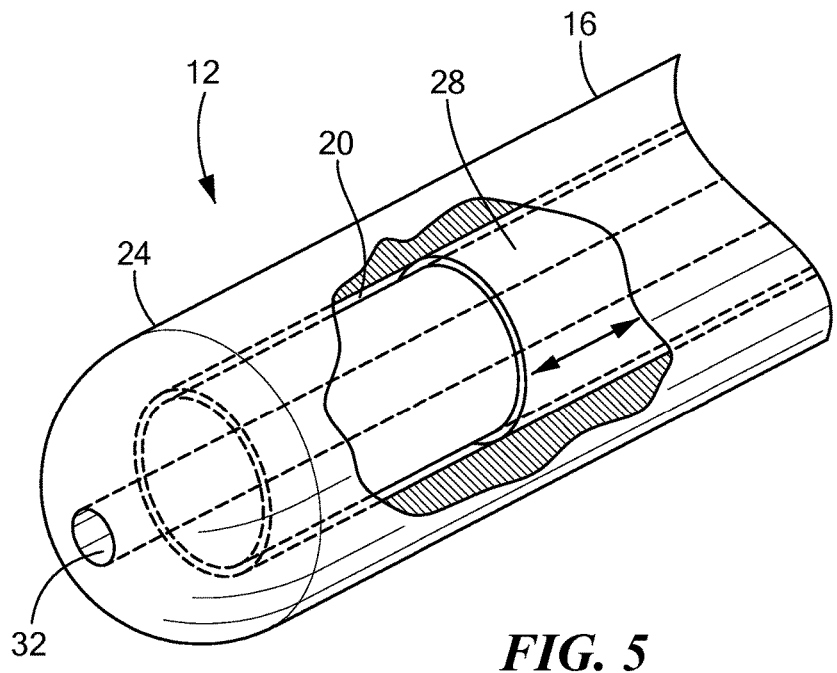
FIG. 5 is a side cross-sectional view of the tunneling tool shown in FIG. 4.

Referring now to FIGS. 4-5, in another configuration, the second lumen 32 is concentric with the first lumen 20 such that the first lumen 20 defines an annular space for the shaping member 28. In particular, the shaping member 28 may be a tubular structure such that it may be slideably received within the first lumen 20. In this configuration, the tip 24 closes the first lumen 20 but leaves open the second lumen 32 for the passage of a lead, guidewire, fluid, needles, and the like. In other configurations, the shaping member 28 may be integrated and affixed into the tunneling such that the tunneling tool 12 defines a single coaxial lumen 28. FIG. 4 illustrates the tunneling tool 12 with the shaping member 28 removed from the first lumen 20. FIG. 5 illustrates the tunneling tool 12 with the shaping member 28 extending partially within the first lumen 20.

Figure 6:
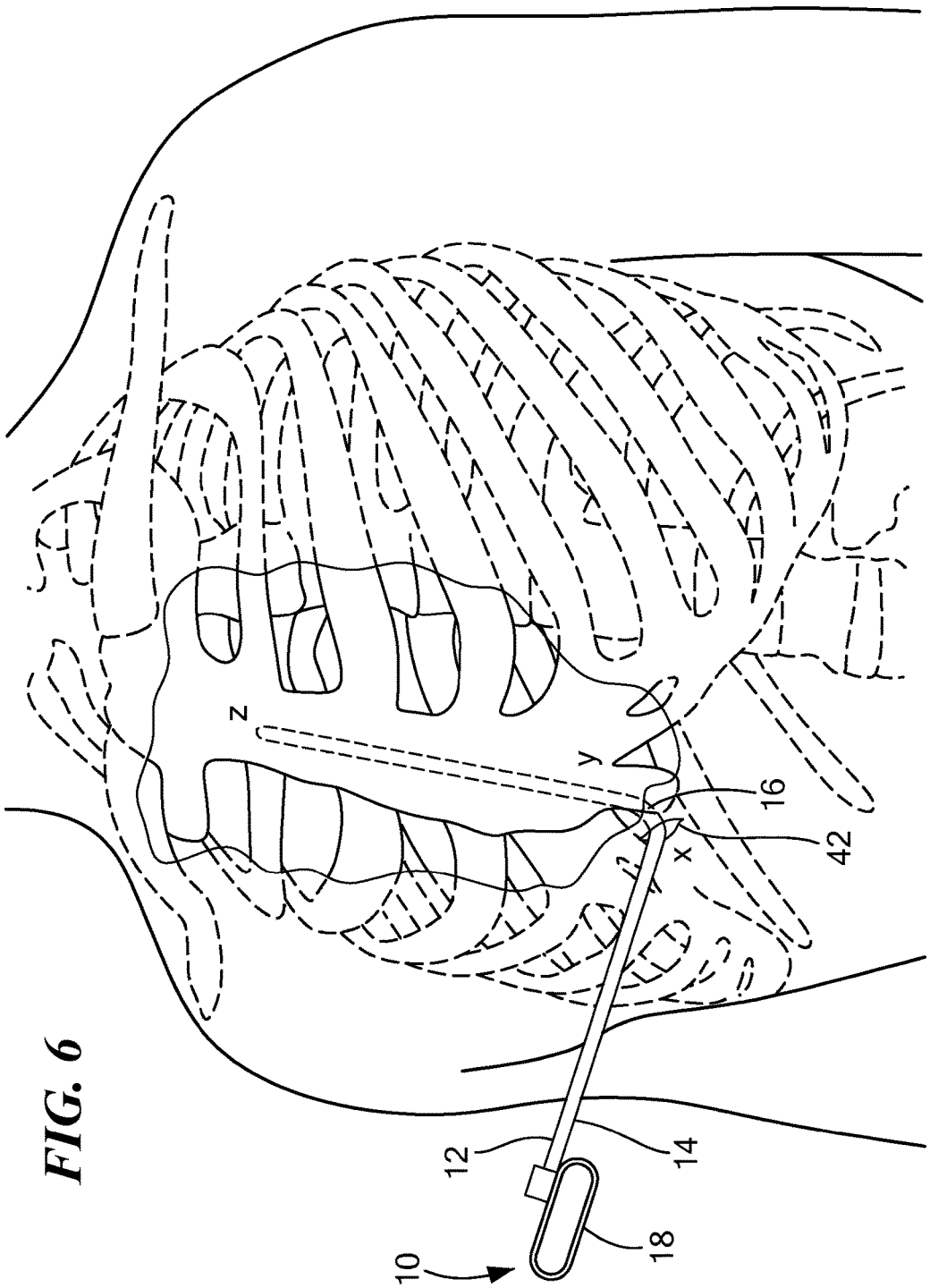
FIG. 6 is a cross-sectional view of a human patient with the tunneling tool shown in FIG. 1 being inserted within the torso of the patient.
Figure 7:
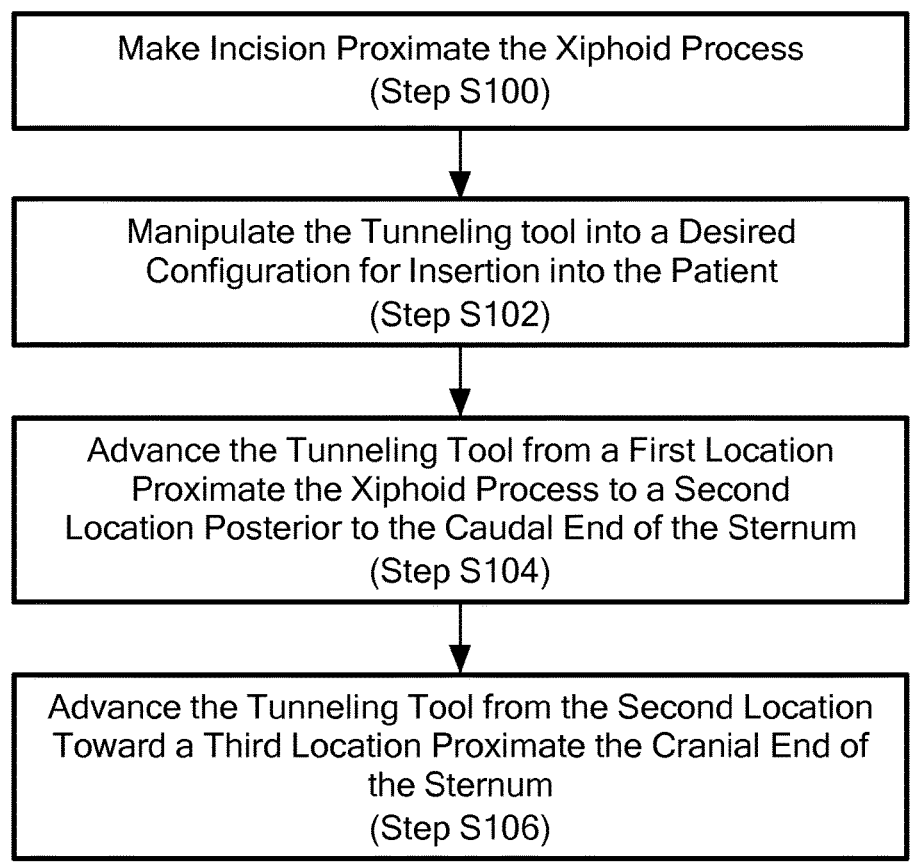
FIG. 7 is a flow chart of an exemplary method of creating a pathway for insertion of a medical lead constructed in accordance with the principles of the present application.

Referring now to FIGS. 6-7, in an exemplary method of use of the medical device 10, the user may make an incision 42 along any portion of the patient's body (Step S100), for example proximate the xiphoid process ("x"), the inferior end of the sternum, or the left or right side of the patient's torso. Although the exemplary method of use is described below with reference to use of the tunneling tool 12 within the patient's torso, it is expressly contemplated that the tunneling tool 12 may be use within any portion of the patient's body, whether subcutaneously, pericardially, or within any anatomical structure of the patient's body. With respect to use of the tunneling tool 12 for placement of a medical lead, the user may manipulate the tunneling to into a desired configuration for insertion into the patient (Step S102). For example, the user may manipulate the distal portion 16 such that the tip 24 is substantially parallel with the major axis of the tunneling tool 12 and facing toward the first opening 22. In such a configuration, the distal portion 16 forms a curved semi-circular configuration and may retain that configuration until manipulated by the user into a different configuration. The curved configuration of the tunneling tool 12, as discussed above, enables the user to traverse the anterior mediastinum tissue without deflection of the distal portion 16 owing to the shaping member 28 being inserted within the first lumen 20. In an exemplary use, the tip 24 may be positioned downward toward the posterior portion of the torso as the tunneling tool 12 is advanced, as shown, for example, in FIGS. 2 and 6, such that tissue is prevented from being lodged within the fourth opening 36 for the second lumen 32 as seen in FIG. 2. The user may advance the tunneling tool 12 from the incision, for example, from a first location proximate the xiphoid process to a second location posterior to the caudal end of the sternum (Step S104) ("y"). The user may then either manipulate the distal portion 16 to a third configuration, for example, a linear configuration to advance the tunneling tool from the second location proximate the inferior end of the sternum to a third location proximate the superior end of the sternum ("z"), or may advance the tunneling tool 12 in the second configuration toward a third location proximate the superior end of the sternum (Step S106). In other configurations, the tunneling tool 12 is advanced from a position proximate the xiphoid process to a position proximate or in contact with the pericardium. When the desired location is reached by the user, the tunneling tool 12 may be detached from the sheath 38 leaving the sheath 38 in place for insertion and placement of a medical lead, for example, a defibrillation lead. In one example, the lead may be advanced through the sheath 38 without the use of a guidewire. In another embodiment, a flexible guidewire (not shown) may be slid through the second lumen 32 when the distal end of the distal portion 16 is advanced toward the desired location within the patient. The tunneling tool 12 may then be withdrawn from the patient leaving the guidewire in place, for example, proximate the superior end of the sternum. A medical lead may then be slid across the guidewire for placement within the patient.

It will be appreciated by persons skilled in the art that the present disclosure is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the tools and techniques described herein, which are limited only by the following claims.

What is claimed is:

1. A medical device, comprising:
   a flexible elongate body defining a proximal end and a distal end, the elongate body defining a first lumen spanning from the proximal end to a location proximal to the distal end;
   a shaping member removeably insertable within the first lumen such that the shaping member and the flexible elongate body are in a first, substantially linear shape, wherein, with the shaping member inserted within the first lumen, the shaping member and the flexible elongate body are configured to be bent from the first shape to a second, substantially curvilinear shape, the shaping member movable to a plurality of locations within the first lumen, wherein the shaping member is configured to retain the flexible elongate body in the second shape when the flexible elongate body and the shaping member are bent from the first shape to the second shape and while the flexible elongate body and the shaping member are tunneled through patient tissue; and
   a tip coupled to the flexible elongate body at the distal end to close the first lumen and extending distally of the distal end, wherein the tip defines a blunted shape and is sized to close the first lumen, wherein the flexible elongate body has a first durometer of hardness, and wherein the tip has a second durometer of hardness less than the first durometer of hardness.

2. The medical device of claim 1, wherein the flexible elongate body is composed of a thermoplastic elastomer.

3. The medical device of claim 1, wherein the shaping member is a stainless steel mandrel.

4. The medical device of claim 1, wherein the flexible elongate body is sized to be insertable within an introducer sheath.

5. The medical device of claim 1, further including a second lumen spanning from the proximal end out through the distal end, and wherein the first lumen and the second lumen are substantially isodiametric.

6. The medical device of claim 5, wherein the second lumen is sized to receive a guidewire.

7. The medical device of claim 1, wherein the blunted shape of the tip is substantially quarter-spherical.

8. The medical device of claim 1, wherein the shaping member spans substantially the entire length of the first lumen.

9. A medical device, comprising:
a flexible elongate body defining a proximal end and a distal end, the elongate body defining a first lumen spanning from the proximal end to a location proximal to the distal end, and a second lumen spanning from the proximal end out through the distal end, the first lumen and the second lumen being disposed in a side-by-side arrangement;
a shaping member within the first lumen such that the shaping member and the flexible elongate body are in a first, substantially linear shape, wherein, with the shaping member within the first lumen, the shaping member and the flexible elongate body are configured to be bent from the first shape to a second, substantially curvilinear shape, the shaping member movable to a plurality of locations within the first lumen, wherein the shaping member is configured to retain the flexible elongate body in the second shape when the flexible elongate body and the shaping member are bent from the first shape to the second shape and while the flexible elongate body and the shaping member are tunneled through patient tissue;
a tip coupled to the flexible elongate body at the distal end to close the first lumen and extending distally of the distal end, wherein the tip defines a blunted shape and is sized to close at least the first lumen; and
the flexible elongate body having a first durometer of hardness, and the tip having a second durometer of hardness less than the first durometer of hardness.

10. The medical device of claim 1, further comprising a second lumen spanning from the proximal end to the distal end and defining an opening at the distal end.

11. The medical device of claim 10, wherein the first lumen and the second lumen are disposed in a side-by-side arrangement.

12. A medical device, comprising:
a flexible elongate body defining a proximal end and a distal end, the elongate body defining a first lumen spanning from the proximal end to a location proximal to the distal end and a second lumen spanning from the proximal end to the distal end and defining an opening at the distal end;
a shaping member insertable within the first lumen such that the shaping member and the flexible elongate body are in a first, substantially linear shape, wherein, with the shaping member inserted within the first lumen, the shaping member and the flexible elongate body are configured to be bent from the first shape to a second, substantially curvilinear shape, the shaping member movable to a plurality of locations within the first lumen, wherein the shaping member is configured to retain the flexible elongate body in the second shape when the flexible elongate body and the shaping member are bent from the first shape to the second shape and while the flexible elongate body and the shaping member are tunneled through patient tissue; and
a tip coupled to the flexible elongate body at the distal end to close the first lumen and extending distally of the distal end, wherein the tip defines a blunted shape and is sized to close the first lumen.

* * * * *